(12) United States Patent
Chou et al.

(10) Patent No.: US 6,796,197 B1
(45) Date of Patent: Sep. 28, 2004

(54) DEVICE AND METHOD FOR SCREENING LIQUID TONERS AND RECEPTORS FOR USE WITH LIQUID TONERS IN ELECTROPHOTOGRAPHY

(75) Inventors: Hsin Hsin Chou, Woodbury, MN (US); Truman Frank Kellie, Lakeland, MN (US); William D. Edwards, New Richmond, WI (US); Brian P. Teschendorf, Vadnais Heights, MN (US)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 10/448,796

(22) Filed: May 30, 2003

(51) Int. Cl.[7] .......................... G01N 11/00; G01N 11/02
(52) U.S. Cl. ........................................ 73/866; 73/150 R
(58) Field of Search ........................... 73/150 R, 53.01, 73/866

(56) References Cited

U.S. PATENT DOCUMENTS

| | | | |
|---|---|---|---|
| 2,990,715 A | * 7/1961 | Bradt ........................ 73/150 R |
| 4,268,598 A | 5/1981 | Leseman et al. ............. 430/107 |
| 4,321,404 A | 3/1982 | Williams et al. ............. 560/115 |
| 4,697,463 A | * 10/1987 | Spooner et al. ............... 73/866 |
| 4,728,983 A | 3/1988 | Zwadlo et al. ................. 355/4 |
| 4,794,651 A | 12/1988 | Landa et al. ................. 430/110 |
| 4,984,532 A | * 1/1991 | Winters ........................ 118/242 |
| 5,115,277 A | 5/1992 | Camis ........................... 355/273 |
| 5,262,259 A | 11/1993 | Chou et al. ..................... 430/47 |
| 5,410,392 A | 4/1995 | Landa ........................... 355/271 |
| 5,886,067 A | 3/1999 | Li et al. ........................ 523/201 |
| 6,103,781 A | 8/2000 | Li et al. ........................ 523/201 |
| 6,255,363 B1 | 7/2001 | Baker et al. ................ 523/201 |

* cited by examiner

Primary Examiner—Robert Raevis
(74) Attorney, Agent, or Firm—Mark A. Litman & Associates, P.A.

(57) ABSTRACT

A testing procedure and method is provided for assessing the quality or acceptability of performance of individual liquid ink electrostatic toners on individual receptor surfaces. An approximately standard drop of the individual liquid toner is placed on the receptor to be tested. The drop is pressed onto the receptor and spread on the surface of the receptor (preferably before the drop has had time to partially evaporate or to have the liquid in the drop absorb or naturally spread on the receptor surface) under controlled conditions. The characteristics of the spread drop on the receptor surface are measured, and the characteristics are compared to parameters defining the characteristics expected from a liquid toner that define acceptable performance between toner and receptor. In this manner the relative performance of individual toners on individual receptor surfaces can be evaluated independent of electrostatic effects. This can be important, as the electrostatic effects bring another parameter of performance into evaluation of the compatibility of the toner and receptor and can misdirect research for adjusting their compatibility.

11 Claims, 5 Drawing Sheets

DEVICE AND METHOD FOR SCREENING LIQUID TONERS AND RECEPTORS FOR USE WITH LIQUID TONERS IN ELECTROPHOTOGRAPHY

FIELD OF THE INVENTION

This invention relates to the field of liquid electrophotography, and specifically to a method and apparatus for screening liquid toners and receptors for use in electrophotographic printing devices.

BACKGROUND OF THE ART

In electrophotographic and electrostatic and imaging processes (collectively electrographic processes), an electrostatic image is formed on the surface of a photoreceptive element or dielectric element, respectively. The photoreceptive element or dielectric element may be an intermediate transfer sheet, drum or belt or the substrate for the final toned image itself, as described by Schmidt, S. P. and Larson, J. R. in Handbook of Imaging Materials, Diamond, A. S., Ed: Marcel Dekker: New York; Chapter 6, pp 227–252, and U.S. Pat. Nos. 4,728,983; 4,321,404; and 4,268,598.

In electrostatic printing, a latent image is typically formed by (1) placing a charge image onto a dielectric element (typically the receiving substrate) in selected areas of the element with an electrostatic writing stylus or its equivalent to form a latent charge image. This latent charge image is developed or toned by (2) applying toner to the charge image, and (3) fixing the toned image. An example of this type of process is described in U.S. Pat. No. 5,262,259.

In electrophotographic printing, also referred to as xerography, electrophotographic technology is used to produce images on a final image receptor, such as paper, film, drums, or the like. Electrophotographic technology is incorporated into a wide range of equipment including photocopiers, laser printers, facsimile machines, and the like.

Electrophotography typically involves the use of a reusable, light sensitive, temporary charge accepting, temporary image receptor, known as a photoreceptor. The photoreceptor is used in the process of producing an electrophotographic image on a final, permanent image receptor. A representative electrophotographic process involves a series of steps to produce a visible toned image on a receptor, including charging of the photoreceptor, exposure to dissipate the charge in an imagewise manner and form a latent charge image, toner development of the latent charge image, transfer of the toned image, fusing of the transferred toned image, cleaning of the photoreceptor, and erasure of residual charge on the photoreceptor.

In the charging step, a photoreceptor is covered with charge of a desired polarity, either negative or positive, typically with a corona device or charging roller. In the exposure step, an optical system, typically a laser scanner or diode array, forms a latent charge image by selectively discharging the charged surface of the photoreceptor in an imagewise manner corresponding to the desired image to be formed on the final image receptor. In the development step, toner particles of the appropriate polarity are generally brought into contact with the latent charge image on the photoreceptor, typically using a developer that is electrically-biased to a potential opposite in polarity to the toner polarity. The toner particles migrate to the photoreceptor and selectively adhere to the latent charge image via electrostatic forces, forming a temporary toned image on the photoreceptor.

In the transfer step, the temporary toned image is transferred from the photoreceptor to the desired final image receptor. An intermediate transfer element is sometimes used to effect transfer of the toned image (usually to accomplish a desired order of color planes in the image) from the photoreceptor with subsequent transfer of the toned image to a final image receptor. In the fusing step, the toned image on the final image receptor is heated to soften or melt the toner particles, thereby fusing the toned image to the final receptor to form a final and permanent image. An alternative fusing method involves fixing the toner to the final receptor under high pressure with or without heat. In the cleaning step, residual toner remaining on the photoreceptor is removed.

Finally, in the erasing step, the photoreceptor charge is reduced to a substantially uniformly low value by exposure to light of a particular wavelength band, thereby removing remnants of the original latent image and preparing the photoreceptor for the next imaging cycle.

Two types of toner are in widespread, commercial use: liquid toner and dry toner. The term "dry" does not mean that the dry toner is totally free of any liquid constituents, but connotes that the toner particles do not contain any significant amount of solvent (or gives the toner a liquid appearance), e.g., typically less than 10 weight percent solvent and preferably less then 8% or less then 5% by total weight of toner (generally, dry toner is as dry as is reasonably practical in terms of solvent content), and the dry toner particles are capable of carrying a triboelectric charge. This relative proportion of liquid carrier is a physical characteristic that distinguishes dry toner particles from liquid toner particles.

A typical liquid toner composition generally includes toner particles suspended or dispersed in a liquid carrier. The liquid carrier is typically a nonconductive dispersant liquid, the lack of charge carrying capability being necessary to avoid discharging the latent electrostatic image. Liquid toner particles are generally solvated or stabilized (dispersed and suspended) to some degree in the liquid carrier (or carrier liquid), typically in more than 50 weight percent (by total weight of the toner) of a low polarity, low dielectric constant, substantially nonaqueous carrier solvent. Liquid toner particles are generally chemically charged using polar groups that dissociate in the carrier solvent, but the toner particles do not carry a triboelectric charge while solvated and/or dispersed in the liquid carrier. Liquid toner particles are also typically smaller than dry toner particles. Because of their small particle size, ranging from about 5 microns to sub-micron size, liquid toners are capable of producing very high-resolution toned images.

A typical toner particle for a liquid toner composition generally comprises a visual enhancement additive (for example, a colored pigment particle) and a polymeric binder. The polymeric binder fulfills functions both during and after the electrophotographic process, supporting the visual enhancement additive during toning and fusing the visual enhancement additive during formation of the permanent image. With respect to processability, the character of the binder impacts charging and charge stability, flow, and fusing characteristics of the toner particles. These characteristics are important to achieve good performance during development, transfer, and fusing. After an image is formed on the final receptor, the nature of the binder (e.g., glass transition temperature, melt viscosity, molecular weight) and the fusing conditions (e.g., temperature, pressure and fuser configuration) impact the durability (e.g., blocking and erasure resistance), adhesion to the receptor, gloss, and the like.

Polymeric binder materials suitable for use in liquid toner particles typically exhibit glass transition temperatures of from about −24° C. to 55° C., which is lower than the range of glass transition temperatures (50–100° C.) typical for polymeric binders used in dry toner particles. In particular, some liquid toners are known to incorporate polymeric binders exhibiting glass transition temperatures ($T_g$) below room temperature (25° C.) to rapidly self fix, e.g., by film formation, in the liquid electrophotographic imaging process; see e.g., U.S. Pat. No. 6,255,363. However, such liquid toners arc also known to exhibit inferior image durability (e.g., poor blocking properties and erasure resistance) resulting from the low $T_g$ after fusing the toned image to a final image receptor.

In other printing processes using liquid toners, self-fixing is not required. In such a system, the image developed on the photoconductive surface is transferred to an intermediate transfer belt ("ITB") or intermediate transfer member ("ITM") or directly to a print medium without film formation at this stage. See, for example, U.S. Pat. No. 5,410,392 to Landa, issued on Apr. 25, 1995; and U.S. Pat. No. 5,115,277 to Camis, issued on May 19, 1992. In such a system, this transfer of discrete toner particles in image form is carried out using a combination of mechanical forces, electrostatic forces, and thermal energy. In the system particularly described in the U.S. Pat. No. 5,115,277 Camis patent, DC bias voltage is connected to an inner sleeve member to develop electrostatic forces at the surface of the print medium for assisting in the efficient transfer of color images.

The toner particles used in such a system have been previously prepared using conventional polymeric binder materials, and not polymers made using an organosol process. Thus, for example the U.S. Pat. No. 5,410,392 Landa patent states that the liquid developer to be used in the disclosed system is described in U.S. Pat. No. 4,794,651 (also to Landa), issued on Dec. 27, 1988. This former Landa patent discloses liquid toners made by heating a preformed high $T_g$ polymer resin in a carrier liquid to an elevated temperature sufficiently high for the carrier liquid to soften or plasticize the resin, adding a pigment, and exposing the resulting high temperature dispersion to a high energy mixing or milling process.

Although such non self-fixing liquid toners using higher $T_g$ ($T_g$ generally greater than or equal to about 60° C.) polymeric binders should have good image durability, such toners are known to exhibit other problems related to the choice of polymeric binder, including image defects due to the inability of the liquid toner to rapidly self fix in the imaging process, poor charging and charge stability, poor stability with respect to agglomeration or aggregation in storage, poor sedimentation stability in storage, and the requirement that high fusing temperatures of about 200–250° C. be used in order to soften or melt the toner particles and thereby adequately fuse the toner to the final image receptor.

To overcome the durability deficiencies, polymeric materials selected for use in both nonfilm-forming liquid toners and dry toners more typically exhibit a range of $T_g$ of at least about 55–65° C. to obtain good blocking resistance after fusing, yet typically require high fusing temperatures of about 200–250° C. to soften or melt the toner particles and thereby adequately fuse the toner to the final image receptor. High fusing temperatures are a disadvantage for dry toners because of the long warm-up time and higher energy consumption associated with high temperature fusing and because of the risk of fire associated with fusing toner to paper at temperatures approximating or approaching the autoignition temperature of paper (233° C).

In addition, some liquid and dry toners using high $T_g$ polymeric binders are known to exhibit undesirable partial transfer (offset) of the toned image from the final image receptor to the fuser surface at temperatures above or below the optimal fusing temperature, requiring the use of low surface energy materials in the fuser surface or the application of fuser oils to prevent offset. Alternatively, various lubricants or waxes have been physically blended into the dry toner particles during fabrication to act as release or slip agents; however, because these waxes are not chemically bonded to the polymeric binder, they may adversely affect triboelectric charging of the toner particle or may migrate from the toner particle and contaminate the photoreceptor, an intermediate transfer element, the fuser element, or other surfaces critical to the electrophotographic process.

In addition to the polymeric binder and the visual enhancement additive, liquid toner compositions can optionally include other additives. For example, charge control agents can be added to impart an electrostatic charge on the toner particles. Dispersing agents can be added to provide colloidal stability, to aid fixing of the image, and to provide charged or charging sites for the particle surface. Dispersing agents are commonly added to liquid toner compositions because toner particle concentrations are high (inter-particle distances are small) and electrical double-layer effects alone will not adequately stabilize the dispersion with respect to aggregation or agglomeration. Release agents can also be used in the toner to help prevent the toner from sticking to fuser rolls when those are used. Other additives include antioxidants, ultraviolet stabilizers, antistatic agents, fungicides, bactericides, flow control agents, and the like.

One fabrication technique used in the manufacture of toners involves synthesizing an amphipathic copolymeric binder dispersed in a liquid carrier to form an organosol, then mixing the formed organosol with other ingredients to form a liquid toner composition. Typically, organosols are synthesized by nonaqueous dispersion polymerization of polymerizable compounds (e.g., monomers) to form copolymeric binder particles that are dispersed in a low dielectric hydrocarbon solvent (carrier liquid). These dispersed copolymer particles are sterically-stabilized with respect to aggregation by chemical bonding of a steric stabilizer (e.g., graft stabilizer), solvated by the carrier liquid, to the dispersed core particles as they are formed in the polymerization. Details of the mechanism of such steric stabilization are described in Napper, D. H., "Polymeric Stabilization of Colloidal Dispersions," Academic Press, New York, N.Y., 1983. Procedures for synthesizing self-stable organosols are described in "Dispersion Polymerization in Organic Media," K. E. J. Barrett, ed., John Wiley: New York, N.Y., 1975.

Liquid toner compositions have been manufactured using dispersion polymerization in low polarity, low dielectric constant carrier solvents for use in making relatively low glass transition temperature ($T_g \leq 30°$ C.) film-forming liquid toners that undergo rapid self-fixing in the electrophotographic imaging process. See, for example, U.S. Pat. Nos. 5,886,067 and 6,103,781. Organosols have also been prepared for use in making intermediate glass transition temperature ($T_g$ between 30–55° C.) liquid electrostatic toners for use in electrostatic stylus printers. See, for example, U.S. Pat. No. 6,255,363 B1. A representative non-aqueous dispersion polymerization method for forming an organosol is a free radical polymerization carried out when one or more ethylenically-unsaturated monomers, soluble in a hydrocarbon medium, are polymerized in the presence of a preformed, polymerizable solution polymer (e.g. a graft stabilizer or "living" polymer). See U.S. Pat. No. 6,255,363.

Once the organosol has been formed, one or more additives can be incorporated, as desired. For example, one or more visual enhancement additives and/or charge control agents can be incorporated. The composition can then subjected to one or more mixing processes, such as homogenization, microfluidization, ball-milling, attritor milling, high energy bead (sand) milling, basket milling or other techniques known in the art to reduce particle size in a dispersion. The mixing process acts to break down aggregated visual enhancement additive particles, when present, into primary particles (having a diameter in the range of about 0.05 to 1.0 microns) and may also partially shred the dispersed copolymeric binder into fragments that can associate with the surface of the visual enhancement additive.

According to this embodiment, the dispersed copolymer or fragments derived from the copolymer then associate with the visual enhancement additive, for example, by adsorbing to or adhering to the surface of the visual enhancement additive, thereby forming toner particles. The result is a sterically-stabilized, nonaqueous dispersion of toner particles having a size in the range of about 0.1 to 2.0 microns, with typical toner particle diameters in the range 0.1 to 0.5 microns. In some embodiments, one or more charge control agents can be added after mixing, if desired.

Several characteristics of liquid toner compositions are important to provide high quality images. Toner particle size and charge characteristics are especially important to form high quality images with good resolution. Further, rapid self-fixing of the toner particles is an important requirement for some liquid electrophotographic printing applications, e.g., to avoid printing defects (such as smearing or trailing-edge tailing) and incomplete transfer in high-speed printing. Another important consideration in formulating a liquid toner composition relates to the durability and archivability of the image on the final receptor. Erasure resistance, e.g., resistance to removal or damage of the toned image by abrasion, particularly by abrasion from natural or synthetic rubber erasers commonly used to remove extraneous pencil or pen markings, is a desirable characteristic of liquid toner particles.

Another important consideration in formulating a liquid toner is the tack of the image on the final receptor. It is desirable for the image on the final receptor to be essentially tack-free over a fairly wide range of temperatures. If the image has a residual tack, then the image can become embossed or picked off when placed in contact with another surface (also referred to as blocking). This is particularly a problem when printed sheets are placed in a stack. Resistance of the image on the final image receptor to damage by blocking to the receptor (or to other toned surfaces) is another desirable characteristic of liquid toner particles.

To address some of these concerns, a film laminate or protective layer may be placed over the surface of the image. This laminate often acts to increase the effective dot gain of the image, thereby interfering with the accuracy of the color rendition of a color composite. In addition, lamination of a protective layer over a final image surface adds both extra cost of materials and extra process steps to apply the protective layer, and may be unacceptable for certain printing applications (e.g., plain paper copying or printing).

Various methods have been used to address the drawbacks caused by lamination. For example, approaches have employed radiation or catalytic curing methods to cure or crosslink the liquid toner after the development step in order to eliminate tack. Such curing processes are generally too slow for use in high speed printing processes. In addition, such curing methods can add significantly to the expense of the printing process. The curable liquid toners frequently exhibit poor self stability and crosslinking can result in brittleness of the printed ink.

Another method to improve the durability of liquid toned images and address the drawbacks of lamination is described in U.S. Pat. No. 6,103,781. This Patent describes a liquid ink composition containing organosols having side-chain or main-chain of crystallizable polymeric moieties. At column 6, lines 53–60, the authors describe a binder resin that is an amphipathic copolymer dispersed in a liquid carrier (also known as an organosol) that includes a high molecular weight (co)polymeric steric stabilizer covalently bonded to an insoluble, thermoplastic (co)polymeric core. The steric stabilizer includes a crystallizable polymeric moiety that is capable of independently and reversibly crystallizing at or above room temperature (22° C.). According to the authors, superior stability of the dispersed toner particles with respect to aggregation is obtained when at least one of the polymers or copolymers (denoted as the stabilizer) is an amphipathic substance containing at least one oligomeric or polymeric component having a weight-average molecular weight of at least 5,000 which is solvated by the liquid carrier. In other words, the selected stabilizer, if present as an independent molecule, would have some finite solubility in the liquid carrier. Generally, this requirement is met if the absolute difference in Hildebrand solubility parameters between the steric stabilizer and the solvent is less than or equal to 3.0 $MPa^{1/2}$.

As described in U.S. Pat. No. 6,103,781, the composition of the insoluble resin core is preferentially manipulated such that the organosol exhibits an effective glass transition temperature ($T_g$) of less than 22° C., more preferably less than 6° C. Controlling the glass transition temperature allows one to formulate an ink composition containing the resin as a major component so that the ink will undergo rapid film formation (rapid self-fixing) in liquid electrophotographic printing or imaging processes using offset transfer processes carried out at temperatures greater than the core $T_g$, preferably at or above 22° C. (Column 10, lines 36–46). The presence of the crystallizable polymeric moiety that is capable of independently and reversibly crystallizing at or above room temperature (22° C.) acts to protect the soft, tacky, low $T_g$ insoluble resin core after fusing to the final image receptor. This acts to improve the blocking problem and erasure resistance of the fused, toned image at temperatures up to the crystallization temperature (melting point) of the crystallizable polymeric moiety.

In attempting to address tack of the image on a final receptor, one must also consider film strength and image integrity. As described in U.S. Pat. No. 6,103,781, for liquid electrophotographic toners (particularly liquid toners developed for use in offset transfer processes), the composition of the insoluble resin core is preferentially manipulated such that the organosol exhibits an effective glass transition temperature ($T_g$) of less than 22° C., and more preferably less than 6° C. Controlling the glass transition temperature allows one to formulate an ink composition containing the resin as a major component so that it will undergo rapid film formation (rapid self-fixing) in printing or imaging processes carried out at temperatures at least the core $T_g$, preferably at or above 22° C. (Column 10, lines 36–46).

As can be seen from the preceding, liquid toners are inherently more complex than dry toners to formulate. After each iteration or formulation, the toners must be tested, or screened, to see how the changes affect actual printing and how well the changed toner will work in an actual printing device. When an electrophotographic system uses dry toner, the measurements of various toner properties can be taken (with multiple testers) and a direct correlation can be inferred to indicate if the toner will perform satisfactorily or not. In liquid electrophotography, the number and interrelationship of the variables is extremely complex. As a result, the current liquid toner screening processes require labor-intensive and time-intensive printing of each liquid toner to be tested on a prototype printing device to determine whether or not a toner will be satisfactory.

A simple screening technique is needed for matching the liquid toner with suitable receptors or vice verse to ensure the print quality from the toner. Furthermore, a liquid toner tends to age and changes its printing performance. A rapid, simple screening technique is needed for quality control to determine if a papery-looking image is due to toner change or receptor property change.

A liquid toner that transfers satisfactorily through a printing device may still fail upon final transfer to the final image receptor (which may be paper, overhead projection film, etc.). As a result, the current liquid toner screening processes require labor-intensive and time-intensive printing of each liquid toner to be tested on a prototype printing device using different final receptors to determine whether or not a toner will be satisfactory. Testing in this way is very inefficient and time-consuming because for each test, the toner to be tested must be poured into the toner cartridge for use. Each test is only minutes long, but once the test is complete, the cartridge must be disassembled and thoroughly cleaned before it can be reassembled and filled with the new toner.

The inclusion of final receptors of various thicknesses and textures may also be difficult because prototype machines are typically not designed to handle a wide variety of materials. Therefore, in order to test various receptors, the prototype machine must frequently be physically modified or rebuilt to accommodate, again resulting in time lost.

SUMMARY OF THE INVENTION

A testing procedure and method is provided for assessing the quality or acceptability of performance of individual liquid ink electrostatic toners on individual receptor surfaces. Rather then performing an actual run of an electrostatic imaging device with the individual toner and the individual receptor, a separate apparatus and method that does not use electrostatic imaging is used to test the interrelated properties of the toner and the receptor under reproducible conditions. An approximately standard drop of the individual liquid toner is placed on the receptor to be tested. The drop is pressed onto the receptor and spread on the surface of the receptor (preferably before the drop has had time to partially evaporate or to have the liquid in the drop absorb or naturally spread on the receptor surface) under controlled conditions. Various characteristics of the spread drop on the receptor surface are measured, and the characteristics are compared to parameters defining the characteristics expected from a liquid toner that define acceptable performance between toner and receptor. In this manner the relative performance of individual toners on individual receptor surfaces can be evaluated independent of electrostatic effects. This independent evaluation can be important as the electrostatic effects bring another parameter of performance into evaluation of the compatibility of the toner and receptor and can misdirect research for adjusting their compatibility.

DETAILED DESCRIPTION OF THE INVENTION

Figure 1:
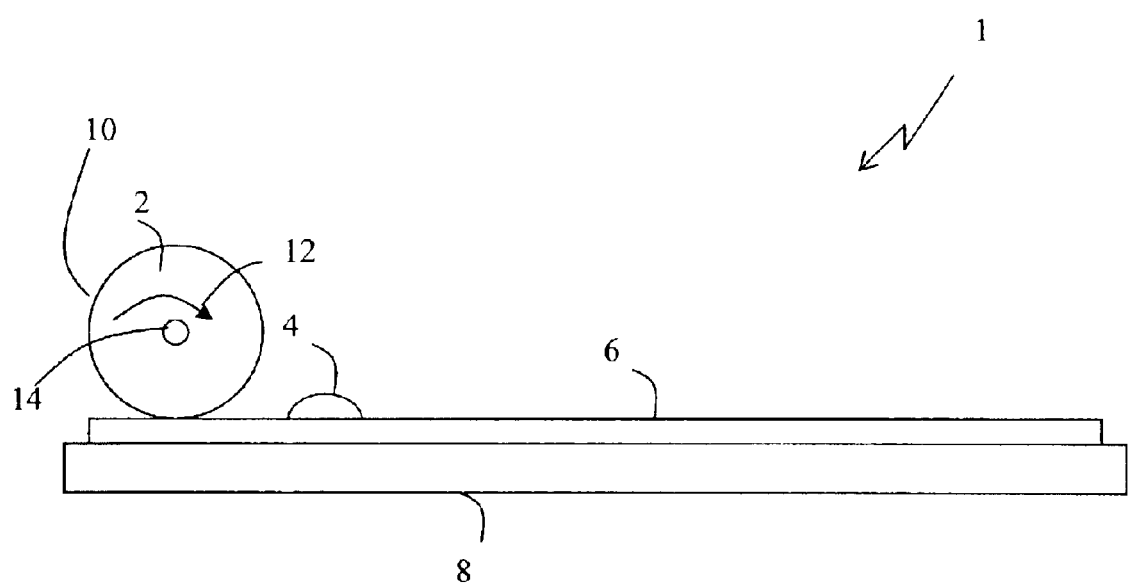
FIG. 1 shows a simplified side view of the basic elements of a screening apparatus that may be used in practicing a method according to the present invention.

The following Definitions are used in the description and practice of the present invention:

"Percent solids" means the ratio of solid toner particles to the total toner liquid. It is determined by weighing a quantity of liquid toner, drying the carrier from the solid portion and re-weighing the solid portion. The second weight divided by the first weight is the "percentage solids" or "percent solids."

"Receptor materials" means a receptor having a printing surface and encompasses both the specific receptor, the composition on the printing surface, and the physical properties (e.g., smoothness, hydrophilicity, porosity, etc.) of that surface.

"Transfer efficiency" means the percentage of the toner image that is transferred from a photoreceptor as compared to the total amount of liquid toner in the total image that was plated on the photoreceptor in a liquid electrophotographic system. That is, the transfer efficiency comprises the amount of liquid toner actually transferred to an electrostatic image from a photoreceptor divided by the total amount of liquid toner that was available within the area of the electrostatic image, An excellent transfer efficiency is >96% (less than 4% of the original toner available within the image area remaining on printer elements).

This invention is a method of testing the interaction between liquid toner and various types of receptor materials, such as paper, coated paper, treated paper, metallized surfaces, synthetic polymer surfaces, natural polymer surfaces, and the like, preferably in the absence of any electrostatic forces. It has been determined that both the composition and texture of paper (and other substrates) plays a key role in how well a toned image on an intermediate transfer member, final transfer member or photoreceptor transfers to that paper as a final substrate. In formulating liquid toners, it is necessary to take into account the effect of the substrate, and especially paper as the substrate on the process of liquid electrophotographic printing. The method of the invention may be practiced with or without the mechanized (motor driven) apparatus.

The invention comprises an apparatus and method for the screening of individual liquid toners and individual toner receptor materials for the purpose of determining how well they will perform in electrophotographic devices. A typical method comprises providing a receptor material to be tested, the receptor having a plurality of edges, and the receptor material having dimensions of width and length and having a first end defined by one edge and a second end defined by a second edge opposite the one edge, the distance between the one edge and the second edge defining the length of the receptor material to be tested. The receptor material is placed on a firm, substantially horizontal, planar supporting surface. At least one individual liquid toner to be tested is provided. One drop of the at least one individual liquid toner is placed near the one end of the receptor material. A compliant roller having a surface is rotated around its axis along the length of the receptor, starting at the first end, rolling the surface of the compliant roller over the drop of liquid toner, and stopping rotation of the compliant roller after the drop has been spread onto the receptor material. This forms an elliptical pattern of toner on the receptor. The characteristics of the elliptical toner pattern is analyzed according to standards identifying relationships of liquid toner properties with respect to the receptor material. The rotational movement of the complaint roller may be driven by at least one of movement of the roller or movement of the rigid surface. The elliptical toner pattern may be analyzed at least by comparing an area of the elliptical pattern to the volume of the drop. For example, the elliptical toner pattern may be analyzed by repeating each test at least three times and averaging the areas of the elliptical pattern from the at least three tests. It is preferred that the drop has a standard volume of from 0.008 to 0.032 cm$^3$. The standards identifying relationships of liquid toner properties with respect to the receptor material are preferably provided in a look-up table, although individuals may be trained for more qualitative visual inspections. The standards identifying relationships of liquid toner properties with respect to the receptor material may thus provided in a series of images. It is helpful to have grid marks visible on the receptor material to assist in defining or visualizing dimensions on the drop after it has been spread. The drop, after it has been spread, can be read by a sensor (e.g., scanner, digital or analog imaging system) and the read drop is quantitatively compared to data (including images) in a look-up table. The method may be practiced wherein the drop, after it has been spread, is read by a sensor and the read drop is quantitatively compared to data in a look-up table using dimensions related to the grid marks in a quantitative comparison. The standards, for example, may include at least one characteristic selected from the group consisting of relative length of a spread drop, relative length/width dimensions of the spread drop, variation in optical density along the length and/or width of the spread drop, and transfer efficiency.

FIG. 1 shows the basic hardware requirements for completing the test. The receptor to be tested 6 is selected and placed on a firm support, such as a table, base or platen 8 (also called herein, when a separate component, a "translating platen"). By "firm" it is meant that the pressure placed on the support (the substrate) during the process will not deform the vertical dimension of the substrate (and if there is a coating layer on the substrate, not deform the coating layer) sufficiently to have more than a 2% variation in drop spreading size as compared to a rigid (e.g., steel sheet) substrate. Clips, guide frames, vacuum or adhesive (not shown) may optionally be used to ensure that the paper does not slide away or move during the test. One drop of the liquid toner to be tested 4 is placed on one end of the receptor 6. The drop volume of each drop is about 0.0166 cm$^3$(+/−0.0016 cm$^3$) or above 0..008 ml (between 0.008 and 0.032 ml). Drop size may vary between and among tests between different liquid toners, but that is part of the testing process, as variations in viscosity will affect both drop size and spread rates. Within a test for a specific liquid toner, it is preferred that drop sizes be as uniform as possible. This can be effected with a pipette or another accurate drop metering system. It is to be noted that these drops are much greater in size than droplets that are ordinarily deposited during a liquid toner electrophotographic ink process, bubble jet process or inkjet process. A compliant roller 10 is provided, having an axis 14 that is sufficiently longer than the roller 10 to be able to grasp the axis and rotate the circumference of the roller along a surface. The compliant roller also has a compliant material 2 that is formed in a circumference around the axis 14, the compliant material being made of one or many compliant layers or blends of polymers or materials, such as elastomers, composites, layered materials, polymer coated materials, polymer saturated papers, foams, and the like. A preferred hardness for the compliant roller is between 20–50 Shore A durometer hardness, although broader ranges can be readily using for the surface conformity characteristics of this component. The compliant roller 10, immediately upon placement of the liquid toner 4 on the receptor 6, is rotated by its axis 14 over the applied toner drop 4, along the paper 6, as shown by arrow 12, creating an oval spread (shown in FIGS. 3a–3c). By "immediately" is meant that there should not be passage of time sufficient to allow significant amounts (e.g., 5% or more) of carrier liquid to evaporate from the drop or to allow the carrier liquid to wick into the surface on which it has been deposited. The rotation of the compliant roller 10 is finished when the roller reaches the end of a defined path of movement, such as the end of the receptor 6, or when the compliant roller 10 is finished creating the oval spread. The roller should not be in contact with the end of the oval spread when the roller is stopped. The rate at which the compliant roller travels the length of the paper may reasonably range from 2–10 inches/second (5.1–25.4 cm/sec). It is relatively important that the speed at which the compliant roller 10 travels the length of the receptor 6 be consistent during the spread and between test samples.

Figure 2:
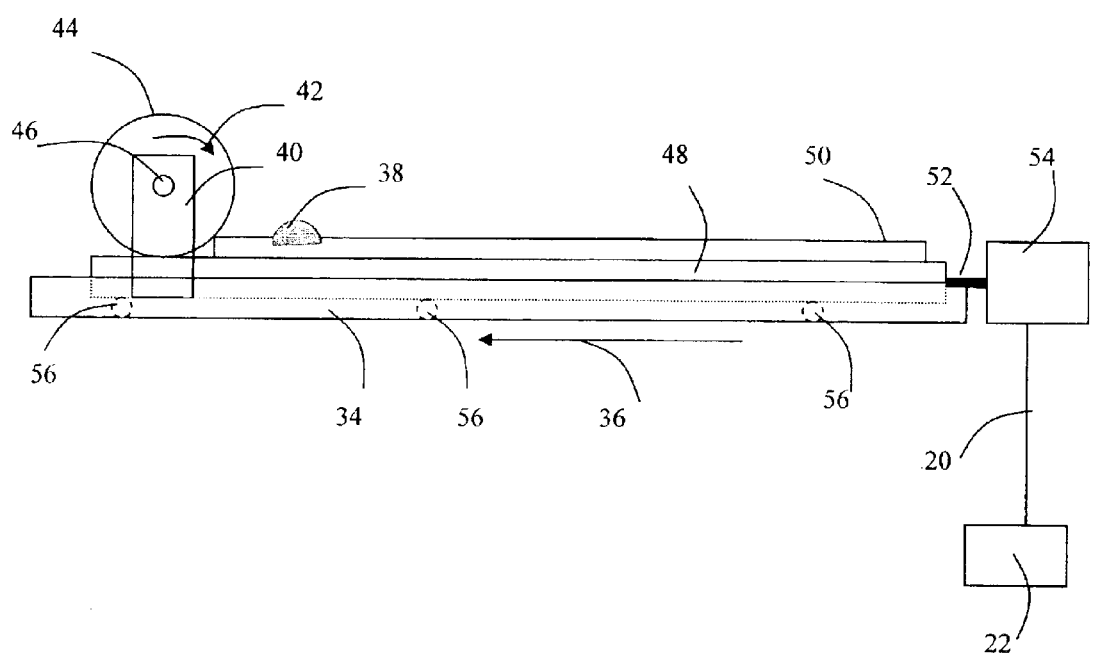
FIG. 2 shows a simplified side view of elements of a modified, mechanized screening apparatus that may be used in practicing a method according to the present invention.

Those skilled in the mechanical arts will know that many of the method steps may be mechanized or power driven. FIG. 2 shows an example of one way to design a simple device to automate the movement of the tester.

In FIG. 2, the compliant roller 44 is held stationary, while the rigid platen 48 travels horizontally 36. The compliant roller 44 maintains intimate contact with the rigid platen 48 and the final receptor 50 throughout the duration of the test.

A frame 40, 34, and 56 may be used to help the compliant roller 44 and the rigid platen 48 work together. Because the compliant roller 44 must maintain intimate, moveable contact with the platen 48 and/or the final substrate 50 thereon, it is necessary to support the compliant roller 44 by its axis 46, which is typically a metal rod, but which may be any rigid material. One skilled in the art would know to use the radius of the compliant roller 44 to determine the distance needed between the axis 46 of the compliant roller 44 and the platen 48. Alternatively, the compliant roller can be spring-loaded against the platen and the force of loading may be adjusted by adjusting the spring constant of the springs. In this embodiment, the axis 46 extends through compliant roller support 40 to support the compliant roller 44, assuring intimate contact with the platen 48. Depending on the size and weight of the compliant roller, it may be necessary for the compliant roller support 40 to either bear some of the compliant roller's 44 weight to avoid excessive force or to apply force by forcing the compliant roller 44 into more intimate contact with the platen 48.

The frame 40, 34, and 56 may also be used to stabilize and mobilize the platen 48. In this embodiment shown in FIG. 2, the platen 48 rides on bearings 56 along tracks 34 (the part of the platen 48 that is behind a track 34 is shown by dashed lines). The direction the platen 48 will move for testing is shown by arrow 36. The compliant roller 44 in intimate contact with the platen 48 will simultaneously rotate in the direction indicated by arrow 42 such that the surface velocity of the compliant roller 44 is equal to the surface velocity of the rigid platen 48.

There are many mechanized means of ensuring smooth horizontal platen 48 movement, including for example: the use of a lead screw, linear motors, stepping motors, pneumatic motors, magnetic drives, stabilizing systems, multiple bearing supports, and the like. These are shown in FIG. 2 as a generic motor 54 that is connected to and can move the platen 48 by a horizontal drive shaft 52. The motor 54 may be connected 20 to a simple on/off switch 22, or it may be controlled by a computer, or other automatic device (not shown).

FIGS. 3a–3e show different transfer patterns obtained from using different liquid toners and different final receptors. The examples below discuss the test method and the corresponding figures.

EXAMPLES

In the following examples, the area of the elliptical image is estimated by measuring the width w and the length d of the spread. The area of an oval (ellipse) is $\frac{1}{4}(\pi wd)$. For an arbitrary comparison unit, we can skip the constant $\frac{1}{4}\pi$ and represent the 'area' by wd, using identical units of dimension (e.g., cm, between comparisons and between any standard and a test).

In the following examples, a single liquid toner was used. A small Teflon pipette capable of delivering approximately $0.0166 \text{ cm}^3$ of liquid toner per drop was used for the testing. The platform speed was set at 3 inches per second.

Referring to FIG. 2, the receptor 50 is positioned on the platen 48 so that the compliant roller 44 is resting on one edge of the receptor 50. One drop of liquid toner 38 is placed on the receptor just in front of the path of the compliant roller 44. In this embodiment, the platen 48 moves and causes the compliant roller 48 to rotate 42 over the surface of the platen, the axel of the compliant roller remaining fixed. It is equally useful to have the roller driven or moved over the surface of a stationary or moving platen. The one toner drop 38 is flattened under the weight of the roller 44 and smeared under the controlled movement and conditions of the device on the receptor 50 to generate an elliptical image on the receptor 50. The motor 54 is pre-programmed to stop the platen 48 once the compliant roller 44 reaches the end of the path or the end of the platen 48 and/or receptor 50. The receptor 50 is removed from the testing device, and the image is fixed to the receptor 50, usually through heat. After fixation the image is examined and measured.

Figure 3A:
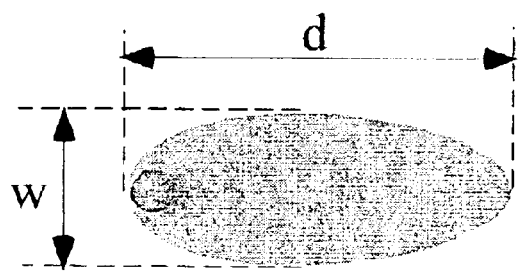
FIGS. 3a–3e show examples of elliptical image patterns obtained using the method and various receptors.

FIG. 3a shows an elliptical image generated on Laser 1000 paper made by Georgia Pacific Papers, Atlanta, Ga. The width "w" of the image is 2.8 cm and the length "d" of the image is 8.1 cm. Using w×d, the Area "A" of the image is $22.68 \text{ cm}^2$.

Figure 3B:

FIG. 3b shows an elliptical image generated on a receptor that was also Laser 1000 paper, but in this example, the paper was coated with a wax polish that alters the oleophilic properties of the paper. In this example, the wax-coated paper was made by rubbing a paraffin wax block against the surface of standard paper. The wax surface was polished smooth with a piece of cotton cloth. The dimensions were w=3.6 cm, d>13.5 cm, and A>48.6 cm². The image length was truncated by the short traveling distance of the platform.

Figure 3C:
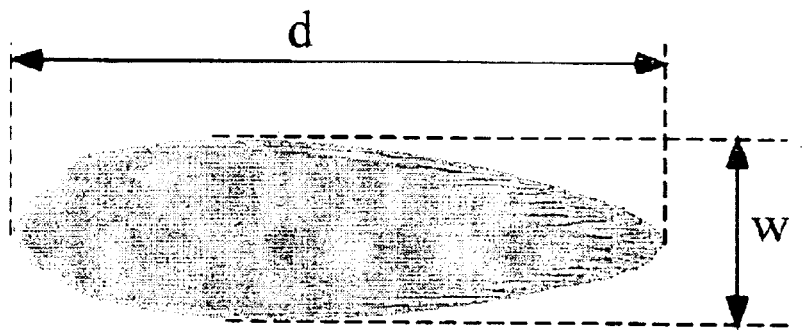

FIG. 3c shows an elliptical image generated on photo quality paper made by Imation Corp. Oakdale, Minn. The dimensions were w=3.45 cm, d=12.1 cm, and A=41.75 cm².

Figure 3D:
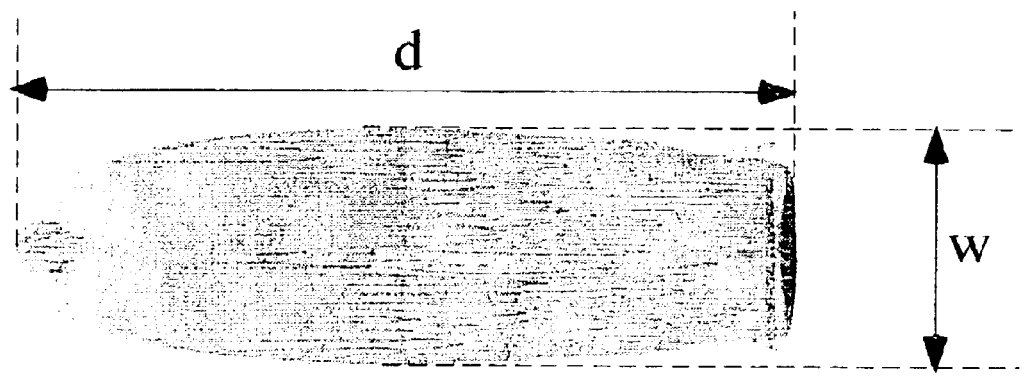

FIG. 3d shows an elliptical image generated on the Laser 1000 paper that had been pre-soaked with the carrier liquid used in the liquid toner. The dimensions were w=3.9 cm, d>13.5 cm, and A>52.6 cm². The image length was truncated by the short traveling distance of the platform.

Figure 3E:
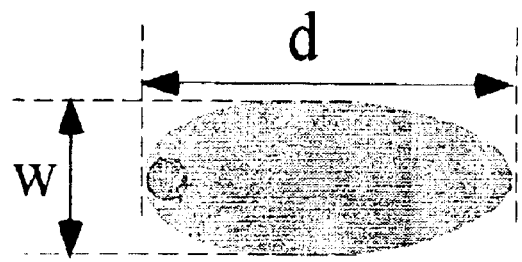

FIG. 3e shows an elliptical image generated on regular bond paper, such as Spectrum™ DP copier paper (manufactured by Georgia-Pacific). The dimensions were w=2.6 cm, d=6 cm, and A=15.6 cm².

Figure 4:
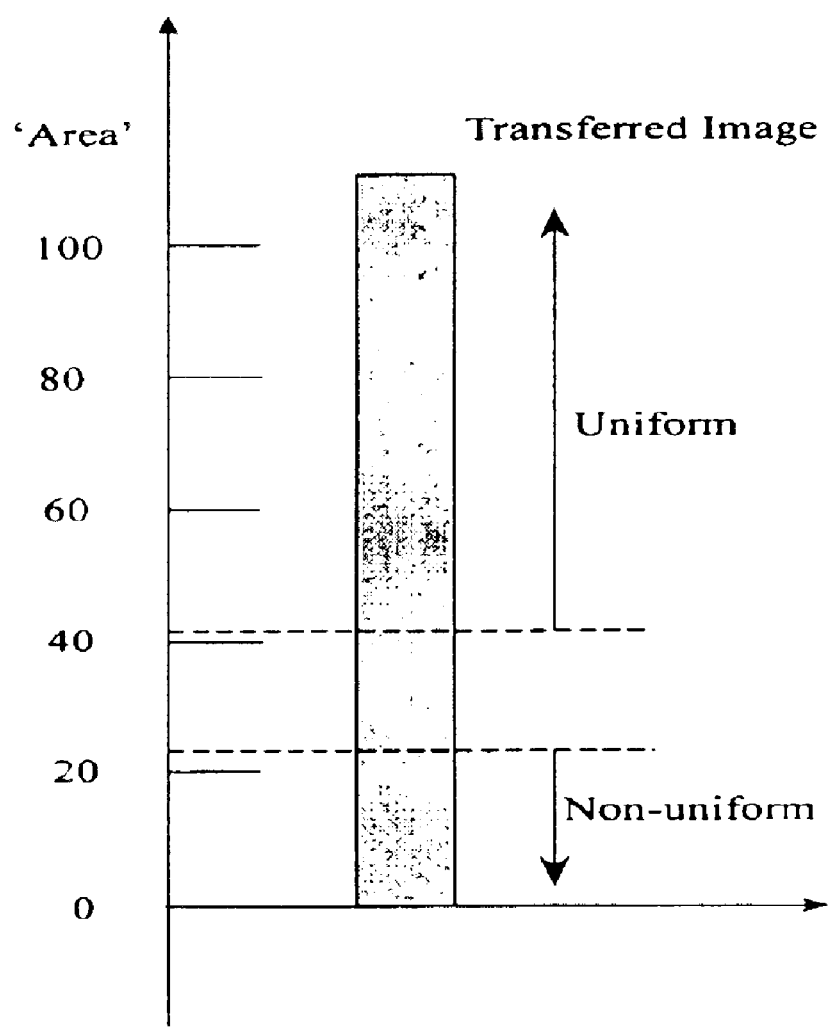
FIG. 4 shows the gray area where some receptors might work with certain liquid toners.

The same ink was then printed in a prototype printer on the same receptors as listed above. For the receptors in FIGS. 3b, 3c, and 3d, the toner transferred uniformly well. For receptors in FIGS. 3a and 3e, the toner did not transfer uniformly. These examples show that a toner/receptor combination that creates an elliptical image with an Area greater than 41 cm² will also work together effectively in a liquid electrophotographic printer. This is shown in FIG. 4. There is a "gray area" where some receptors might work with certain liquid toners, even if the elliptical image pattern is low.

Example 2

Liquid toners of varying compositions will be absorbed into different receptors at different rates. The rate at which a toned image loses impregnated carrier liquid to absorption by the receptor will affect the transfer efficiency of the image. The screening apparatus can also determine how rapidly the liquid carrier will be absorbed from a plated image.

First, the average drop volume was measured for each toner. Then the toner was dropped on the receptor as described above for spreading. Each test was run at a platen speed of 3 inches per second (7.6 cm/sec.). Each resulting image was fused and the test was repeated four times (providing five total runs). Repeating the test at least three times is desirable. For each test, the area of the ellipse was calculated and the average of all five areas obtained. By computing the ratio of the average drop weight and the average area, an "absorption" figure was reached (in mg/cm²). Rapid absorption of carrier liquid from toner into the receptor is one indication that the transfer efficiency of the toner in a printer to that specific receptor will be low. An alternative test is to have the drop remain on the receptor surface for a specific amount of time (e.g., 5, 10, 15, 20, 30 seconds or one minute) at standard conditions (e.g., standard temperature, standard pressure and 50% RH) and then perform the spreading test. This controlled time parameter will emphasize effects of absorption of the carrier liquid into the receptor.

All tests should be compared to a standard of results. The standard may be visual images or a look-up table. The look-up table may be a physical look-up table (having images of measurements with which the tests should comply) or can be an electronic look-up table, with spread results electronically imaged and compared to the look-up table. It is also possible to print a grid onto the receptor surface to assist in taking measurements, the material from the printed grid image being very small and thin and of a material that will not greatly impact the absorption and spreading of the liquid toner on the surface of the receptor. Alternatively a pattern may be printed on the backside of the receptor that will show through the receptor to provide the pattern.

Many optional variations may be performed on the process and apparatus of the present invention and remain within the broad concepts of the invention taught herein and claimed in this Patent.

What is claimed is:

1. A method of screening individual liquid toners for electrophotographic printing devices and receptor material with respect to the how well the individual liquid toners work with the receptor materials, comprising the steps of:
   providing a receptor material to be tested, the receptor having a plurality of edges, and the receptor material having dimensions of width and length and having a first end defined by one edge and a second end defined by a second edge opposite the one edge, the distance between the one edge and the second edge defining the length of the receptor material to be tested;
   placing the receptor material on a firm, substantially horizontal, planar supporting surface;
   providing at least one individual liquid toner to be tested;
   placing one drop of the at least one individual liquid toner near the one end of the receptor material;
   rotating a compliant roller having a surface around its axis along the length of the receptor, starting at the first end, rolling the surface of the compliant roller over the drop of liquid toner, and stopping rotation of the compliant roller after the drop has been spread onto the receptor material to form an elliptical pattern of toner on the receptor; and
   analyzing the characteristics of the elliptical toner pattern according to standards identifying relationships of liquid toner properties with respect to the receptor material.

2. The method of claim 1 wherein the rotational movement of the complaint roller is driven by at least one of movement of the roller or movement of the rigid surface.

3. The method of claim 1 wherein the elliptical toner pattern is analyzed at least by comparing an area of the elliptical pattern to the volume of the drop.

4. The method of claim 1 wherein the elliptical toner pattern is analyzed by repeating each test at least three times and averaging the areas of the elliptical pattern from the at least three tests.

5. The method of claim 1 wherein the drop has a volume of from 0.008 to 0.032 $cm^3$.

6. The method of claim 1 wherein the standards identifying relationships of liquid toner properties with respect to the receptor material are provided in a look-up table.

7. The method of claim 1 wherein the standards identifying relationships of liquid toner properties with respect to the receptor material are provided in a series of images.

8. The method of claim 1 wherein grid marks are visible on the receptor material to assist in defining or visualizing dimensions on the drop after it has been spread.

9. The method of claim 1 wherein the drop after it has been spread is read by a sensor and the read drop is quantitatively compared to data in a look-up table.

10. The method of claim 8 wherein the drop after it has been spread is read by a sensor and the read drop is quantitatively compared to data in a look-up table using dimensions related to the grid marks in a quantitative comparison.

11. The method of claim 1 wherein the standards include at least one characteristic selected from the group consisting of relative length of a spread drop, relative length/width dimensions of the spread drop, variation in optical density along the length and/or width of the spread drop, and transfer efficiency.

* * * * *